US005922593A

United States Patent [19]

Livingston

[11] Patent Number: 5,922,593

[45] Date of Patent: Jul. 13, 1999

[54] MICROBIOLOGICAL TEST PANEL AND METHOD THEREFOR

[75] Inventor: Dwight Livingston, Fallston, Md.

[73] Assignee: Becton, Dickinson and Company, Franklin Lakes, N.J.

[21] Appl. No.: 08/863,045

[22] Filed: May 23, 1997

[51] Int. Cl.[6] .............................. C12M 1/20; C12Q 1/24

[52] U.S. Cl. .......................... 435/288.5; 435/30; 435/33; 435/287.7; 435/309.1; 422/102; 422/58; 422/100; 436/165

[58] Field of Search ................................ 435/29, 30, 33, 435/40, 287.7, 288.5, 288.4, 288.7, 305.2, 305.3, 309.1; 422/58, 61, 102–104, 100; 436/165, 180

[56] References Cited

U.S. PATENT DOCUMENTS 3,963,355 6/1976 Aldridge, Jr. et al. ................. 356/201
4,038,151 7/1977 Fadler et al. ............................ 195/127
4,195,060 3/1980 Terk ........................................... 422/61
4,599,315 7/1986 Terasaki et al. ........................ 435/301
4,806,316 2/1989 Johnson et al. ......................... 422/100
5,035,866 7/1991 Wannlund ............................... 422/102
5,182,082 1/1993 Monthony et al. ....................... 422/57

*Primary Examiner*—William H. Beisner
*Attorney, Agent, or Firm*—Fitzpatrick, Cella, Harper & Scinto

[57] ABSTRACT

A microbiological test panel assembly used in microorganism identification (ID) and antimicrobial susceptibility determinations (AST) testing is provided. The microbiological test panel assembly includes a plurality of test wells segregated into two sections. The test wells of each section are adapted to receive reagents capable of causing reactions used in performing ID and AST testing. The reagents enter the respective sections through fill ports and flow down a passageway of the test panel assembly in a serpentine manner filling all the test wells.

17 Claims, 13 Drawing Sheets

MICROBIOLOGICAL TEST PANEL AND METHOD THEREFOR

BACKGROUND OF THE INVENTION

Field of the Invention

This invention relates to the field of test panels or trays. More particularly, the present invention provides a microbiological test panel having a plurality of sample wells segregated into two sections so that test samples and reagents used for microorganism identification (ID) and antimicrobial susceptibility testing (AST) can be placed therein.

Known test trays are used for performing tests on microbiological samples related to patient diagnosis and therapy. The microorganism samples may come from a variety of sources, including infections, bodily fluids and abscesses. From those microorganism samples an inoculum is prepared in accordance with established procedures which produce a bacterial or cellular suspension of a predetermined concentration. The inoculum is then used, for example, in ID testing to determine the types of microorganisms present in a patient's sample.

In ID testing, reagents are typically placed in cupules, or test sample wells, contained in ID test trays. Alternatively, paper disks with reagents may be placed in those wells. In the presence of an actively fermenting culture of microorganisms in the inoculum, the reagents may change color, cause turbidity or grow into a formation of a predetermined shape. By examining the reaction of the inoculum and reagents over a period of time, or lack thereof, and comparing that reaction to known reactions, the types of microorganisms can be identified.

However, filling test wells one-by-one with the required inoculum and reagents is tedious, time-consuming and messy. Moreover, any delay in the identification process will cause a delay in diagnosis and treatment to the detriment of the patient. Delays may still result even if a reagent dispensing pipette is used to fill the test wells. For example, when a multi-nozzle pipette, or other type of dispensing apparatus, is used to dispense reagents into a group of test wells, the test wells must be place directly underneath the nozzle so that each is filled properly. This process has many of the same drawbacks as when each well is manually filled. For example, manual placement of the test tray under the nozzles is time consuming and the possibility of misalignment between them exists.

Other microbiological test trays have been used for AST testing of microorganisms. AST testing is used to determine the susceptibility of a microorganism in an inoculum to various therapeutics, such as antibiotics. Based on the test results, physicians can then, for example, prescribe an antimicrobial product which will be successful in killing that microorganism.

Test wells of AST test trays are filled with reagents, in similar fashion to ID testing, and concentrations of antibiotics. Accordingly, the same problems are encountered as discussed with filling the wells for the ID test trays.

The ID/AST testing usually requires that the test trays be incubated at a controlled temperature for an extended period of time. This allows the reaction between the inoculum and reagent to occur as the microorganisms process biologically the reagents mature and stabilize. At predetermined time intervals, each well of the test tray is examined for an indication of color change, turbidity, or the growth of a formation of a predetermined shape. This is a long and tedious process when done manually by a technician.

This process of examining the wells of the test trays is made even longer and more tedious because AST and ID tests typically require using separate test trays, i.e., one tray for each type of test. Thus, even when the same microorganism sample is to be ID and AST tested, the technician would need to keep track of and record the reaction results for at least two separate test trays.

Some attempts have been made to address the problems discussed above, but they have failed. Some of these attempts require complicated procedures such as using a bell chamber to create a negative vacuum so that wells within a test tray can be filled with reagents via a maze of tunnels. Other attempts require the user to follow multiple and arduous steps to fill the wells of a test tray, as well as requiring the user to complete assembly of the test tray. Additional descriptions of other known test trays and ID/AST testing devices can be found in U.S. Pat. Nos. 5,182,082, 4,038,151, and 3,963,355, incorporated herein by reference.

Accordingly, there is a need for a test tray that solves the above described problems. In particular, there is a need for a single microbiological test tray in which all the test wells contained therein can be easily and conveniently filled with the reagents, inocula and therapeutics required for both AST and ID testing without the complicated steps of filling or assembly of the test tray.

SUMMARY OF THE INVENTION

The present invention solves the foregoing deficiencies by providing microbiological test panel have a plurality of test wells that can be easily and conveniently filled with reagents used for simultaneous ID and AST testing.

In particular, one aspect of the present invention is directed to a microbiological test panel including a base including a planar surface having a plurality of translucent cups extending from a first side of the planar surface, and a side wall extending from the first side in the same direction as the cups; and a chassis including a planar surface having a plurality of open-ended tubes formed on a first side of the chassis. The bottom end of each tube is located on the planar surface. The top end of each tube has an indented portion to engage one of the translucent cups so as to form a well when the chassis is press-fit into the base to form a chassis-base subassembly. The chassis also includes a plurality of raised passage walls on a second side of the planar surface. The passage walls forms a passageway over the openings at the bottom ends of the tubes. One end of the passageway has an opening to allow an inoculum to flow through the passageway. The other end of the passageway has an opening to allow excess inoculum to a reservoir formed at a first end of the chassis. The chassis also includes an absorbing member positioned in the reservoir to absorb the excess inoculum. The chassis further comprising an air communication port between the first side and the second side of the planar surface of the chassis. The air communication port is formed as an open-ended tube extending from the second side of the planar surface. The microbiological test panel also includes a lid attached to the chassis-base subassembly over the second side of the chassis so as cover the chassis-base assembly. The lid has a planar surface for covering the plurality of wells, a reservoir at a first end of the lid to receive the absorbing member of the chassis, and an entry port at a second end of the lid to receive the inoculum into the passageway.

In accordance with another aspect of the present invention, the microbiological test panel has a chassis having two separate sections which contain test wells for ID and AST testing, respectively.

Yet another aspect of the present invention is directed to a method for inoculating a microbiological test panel having a base, chassis and lid as described above. The method includes the steps of holding the microbiological test panel at an incline to the horizontal plane so that the entry port is in an elevated position, inserting inocula into the entry port, waiting while the inocula flows down the passageway filling all the enclosures, and allowing the excess inocula to be absorbed by the pad.

Other aspects of the present invention are described in more detail below.

BRIEF DESCRIPTION OF THE DRAWINGS

These and other features and advantages of the present invention can best be understood by reference to the detailed description of the preferred embodiments set forth below taken with the drawings in which.

DETAILED DESCRIPTION OF THE PREFERRED EMBODIMENTS

Figure 1:
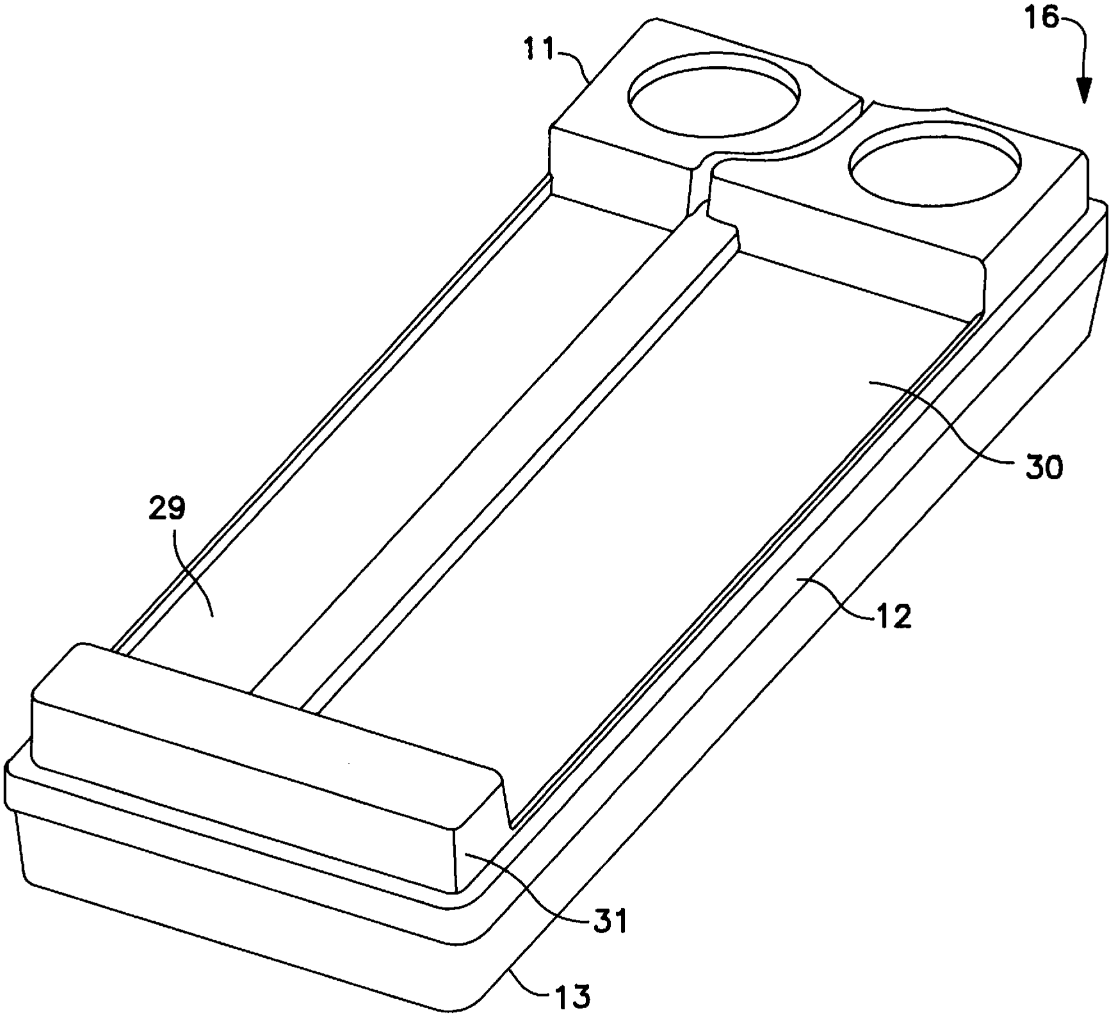
FIG. 1 is a perspective view of an microbiological test panel assembly of the present invention.

Referring to the drawings, there is illustrated a device according to the present invention for receiving and storing reagents and test samples to be tested and analyzed.

The preferred embodiment of a microbiological test panel assembly 10 according to the present invention includes a lid 11, a chassis 12, and a base 13, as shown in FIG. 1 and FIGS. 7A–C.

Figure 2A:
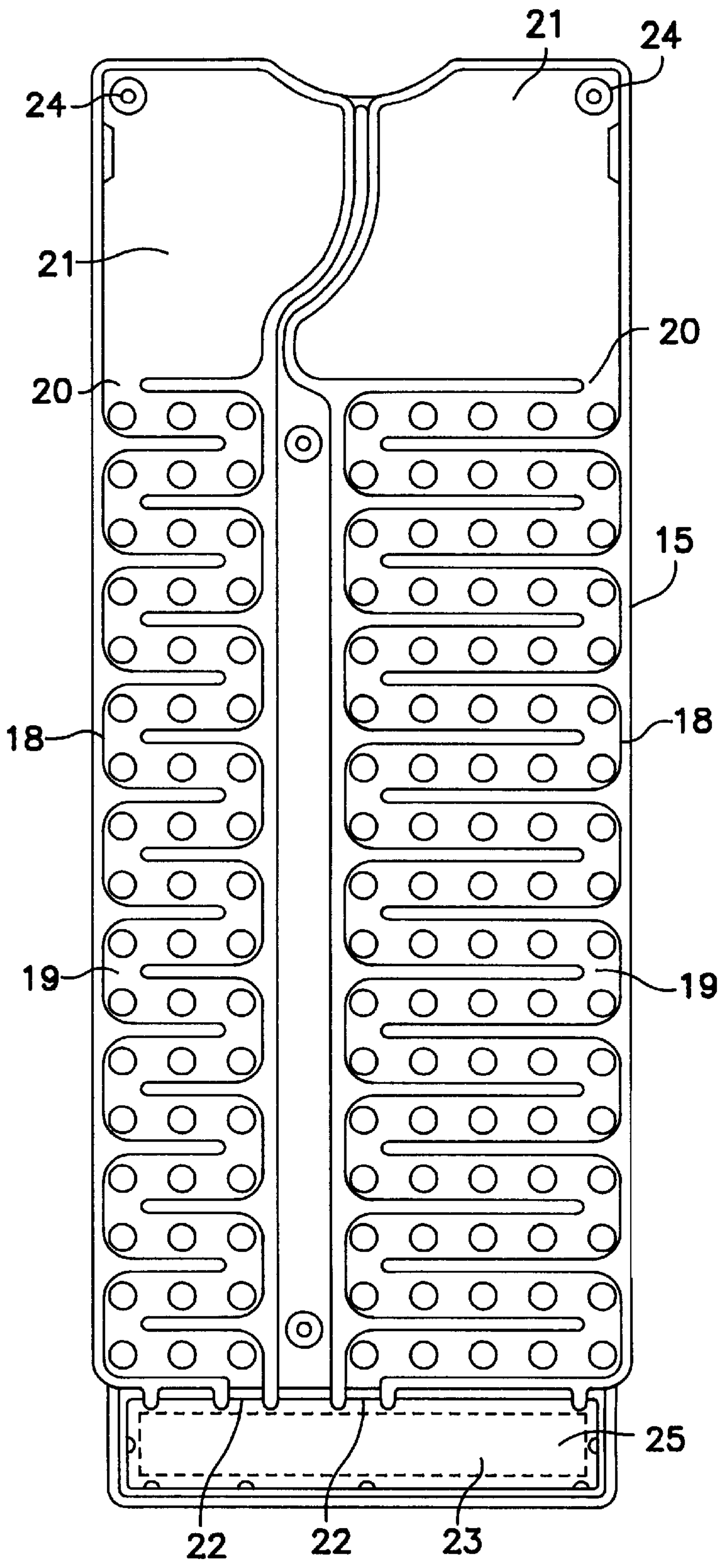
FIGS. 2A and 2B are top and bottom views of the chassis of the present invention.
Figure 2B:
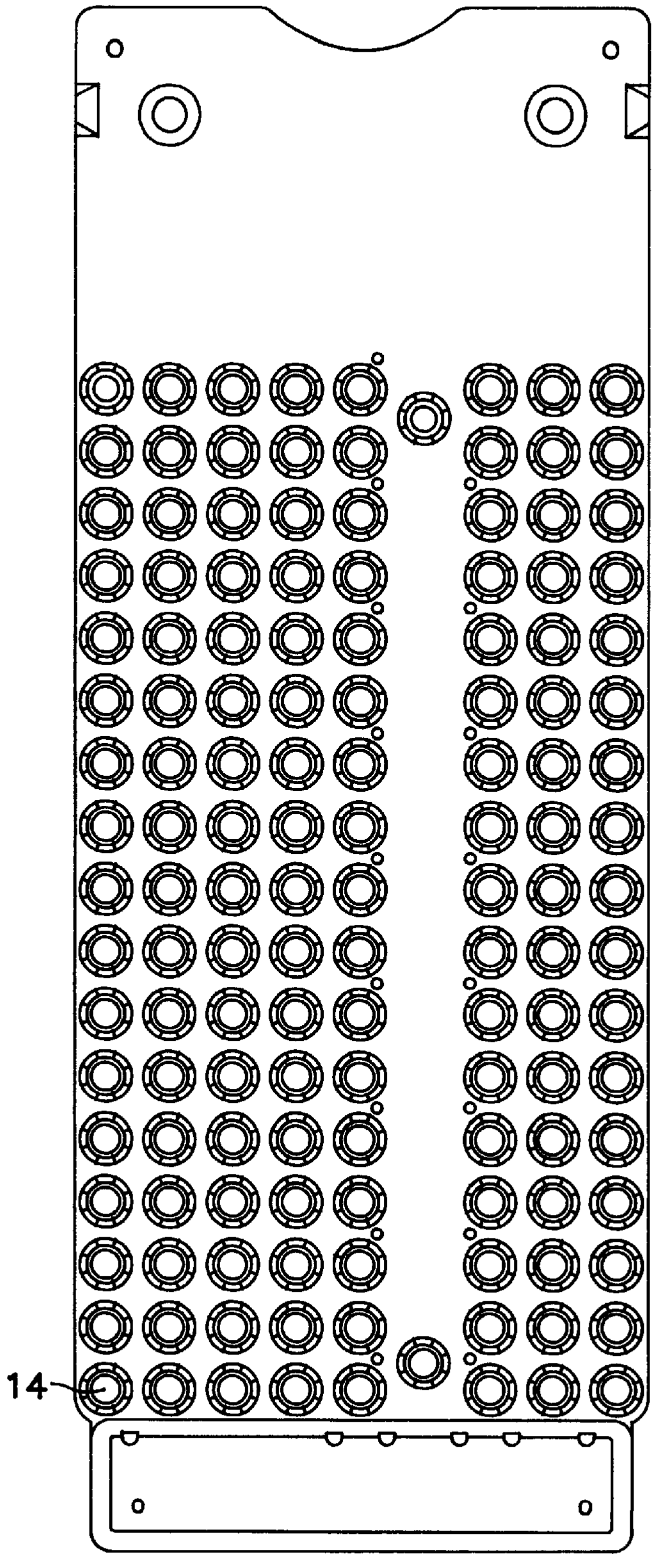

A plurality of test wells 14 are formed when the base 13 and chassis 12 are in contact with each other to form a chassis-base subassembly (one test well 14 is shown in FIGS. 3A–3D). The chassis can be press-fit to the base 13 to form this contact. Press-fitting improves the assembly precision of the present invention, reduces potential leakage problems and permits closer spacing or arrangement of the test wells 14. The test wells 14, as shown in FIG. 2B, are arranged in an array of rows and columns, but other arrangements of test wells are possible.

The chassis 12 comprises a planar surface 15 (shown in FIGS. 2A and 2B) having a plurality of open-ended tubes 16 (one of which is shown in FIGS. 3A–3D) formed on a first side of the planer surface 15. The bottom end of each tube 16 is located on the planar surface 15. The top end of each tube 16 extends away from the planer surface 15 and has an indented band 17.

Each tube 16 is substantially perpendicular to the planer surface 15 to form a substantially sharp edge at the junction of the tube 16 and the planar surface 15. This sharp edge prevents inoculum from escaping each test well 14 after it has been filled. Preferably, the tube 16 is tapered with the interior of the indented band 17 having approximately a 1 degree draft and the remaining interior having a 2 degree draft. The exterior of the indented band 17 of each tube 16 has at 35 least one vertical rib 17*a* (shown in FIG. 3D). This provides a mechanism of ventilating the test wells 14 as described in more detail below.

The chassis 12 also has a plurality of raised passage walls 18 on a second side of the planar surface 15. The passage walls 18 form one or more serpentine passageways 19 on the second side of the planer surface 15. For example, as illustrated in FIG. 2A, two serpentine passageways 19 are shown, but any number of passageways may be provided as needed. Each serpentine passageway 19 is positioned over a predetermined plurality of openings at the bottom ends of the tubes 16. One end of each serpentine passageway 19 has an opening 20 into a respective chamber 21 (as shown in FIGS. 6A–I). The chambers 21 are formed when the lid 11 is connected to the chassis-base subassembly as discussed below.

Each chamber 21 includes a snorkel 24 which provides an air vent between the lid 11 and the chassis-base subassembly. The snorkels 24 are an open-ended tube extending from the second side of the planer surface 15.

The other end of each serpentine passageway 19 has an opening 22 to a reservoir 23 (as shown in FIGS. 6A–6I). Preferably a pad 25 is inserted into the reservoir 23. The pad 25 can be formed of a cellulose acetate material. Of course, other materials for absorbing members can be used as will be appreciated by one skilled in the art. The serpentine passageways 19 led into the reservoir 23 as shown in FIG. 2A.

Preferably, the chassis 12 is constructed of a molded plastic material, but other types of material can be used. The chassis 12 has a rectangular shape with a notched portion at one end. The notched portion is merely used to indicate the top of the test panel assembly 10. Other shapes for the chassis 12 may be used to suit specific applications or needs. Preferably, the material used in constructing the chassis 12 is opaque, so as to prevent transmission of light therethrough. An opaque chassis has been found to improve performance of gathering test data when the test panel assembly 10 is used in conjunction with an automated microbiological testing apparatus.

Figure 5A:
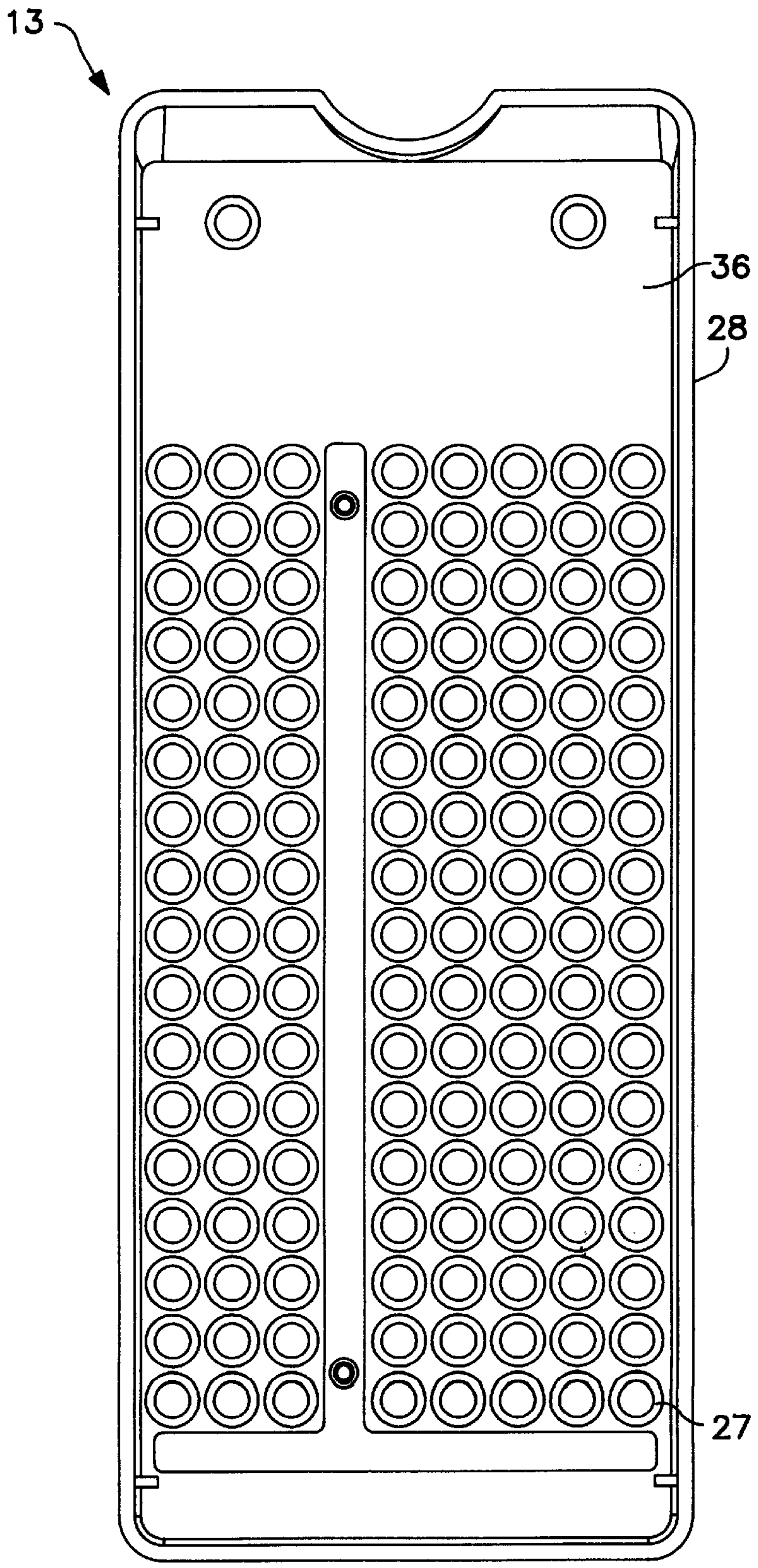
FIGS. 5A and 5B are top and bottom views of the base of the present invention.
Figure 5B:
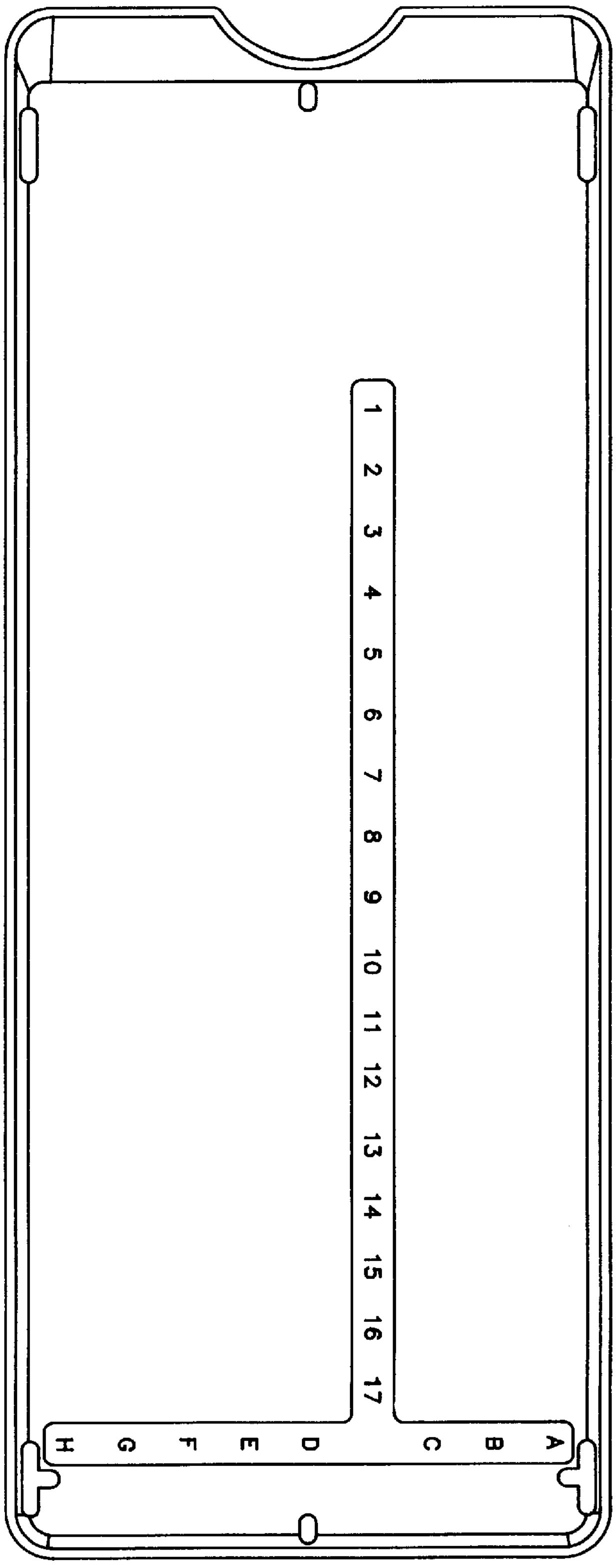
Figure 6A:
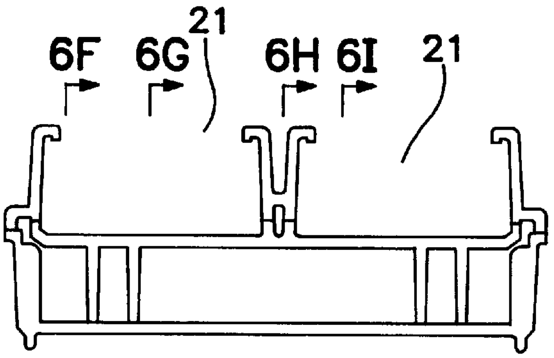
FIGS. 6A–6I are sectional views of the microbiological test panel of FIG. 1 taken along various reference lines.
Figure 6B:
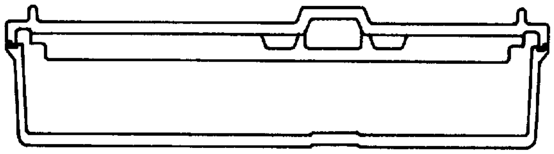
Figure 6C:
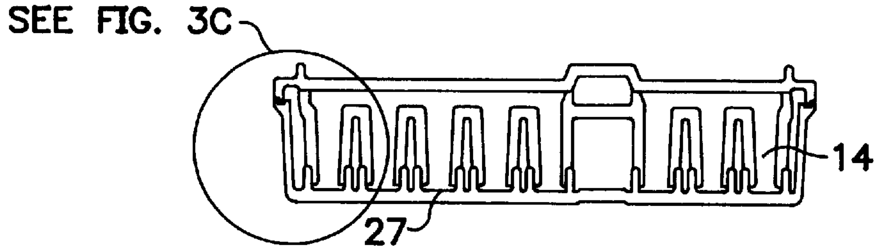
Figure 6D:
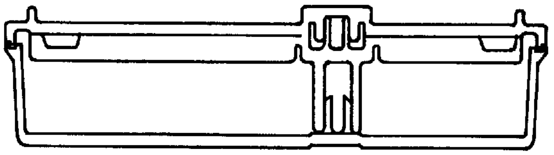
Figure 6E:
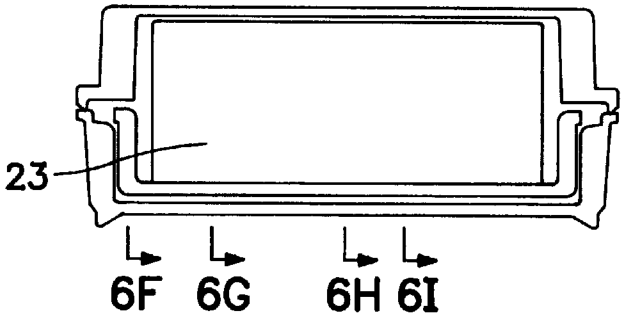
Figures 6F, 6G, 6H, 6I:
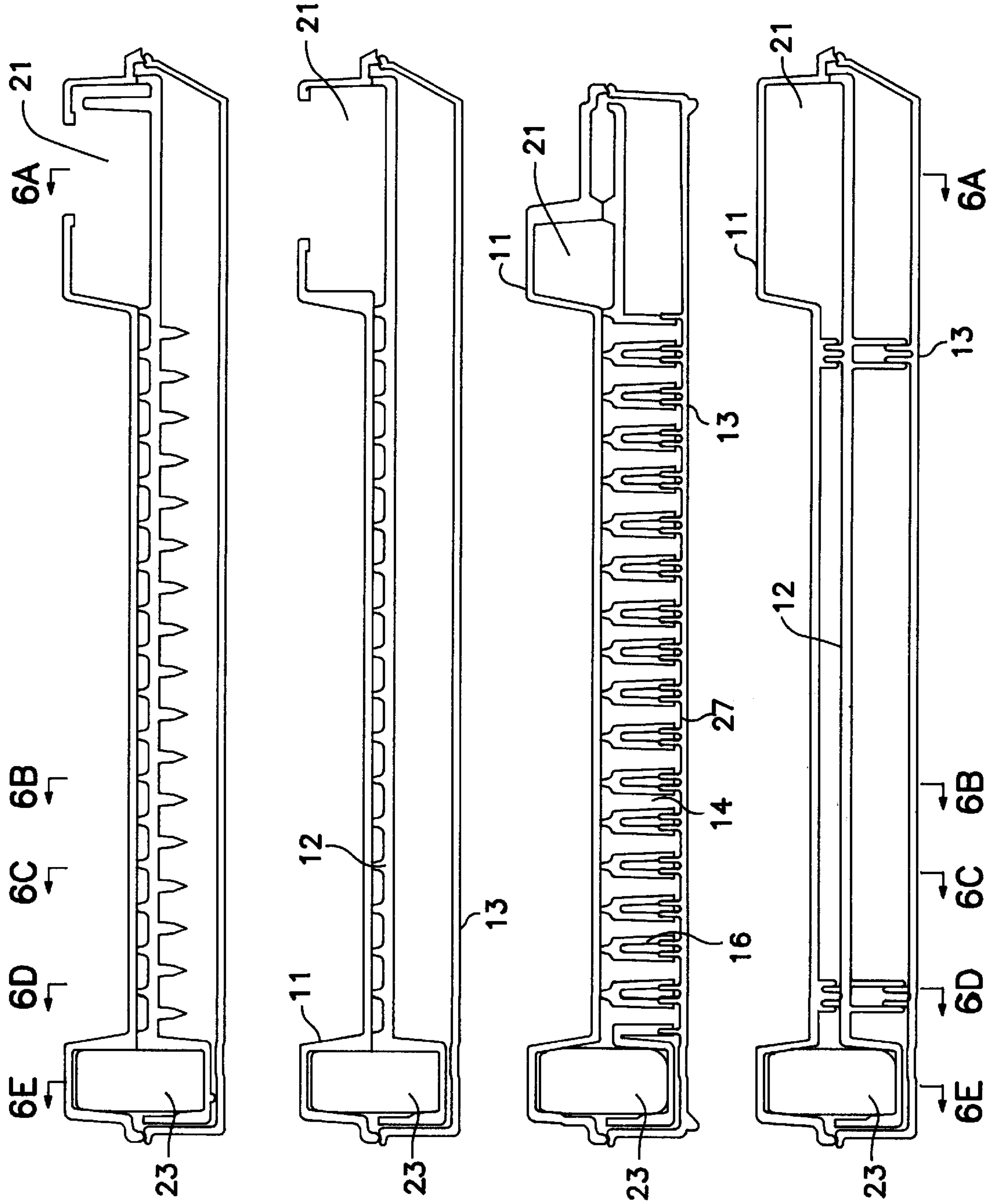
Figure 7C:
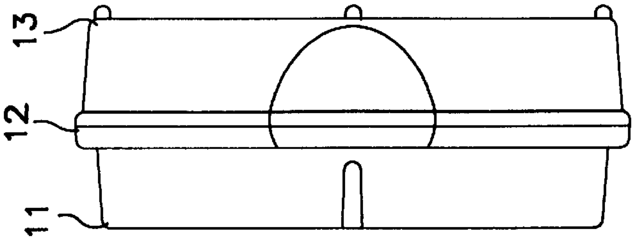
FIGS. 7A–7C are top, front and end views of the microbiological test panel assembly of FIG. 1.
Figure 7A:
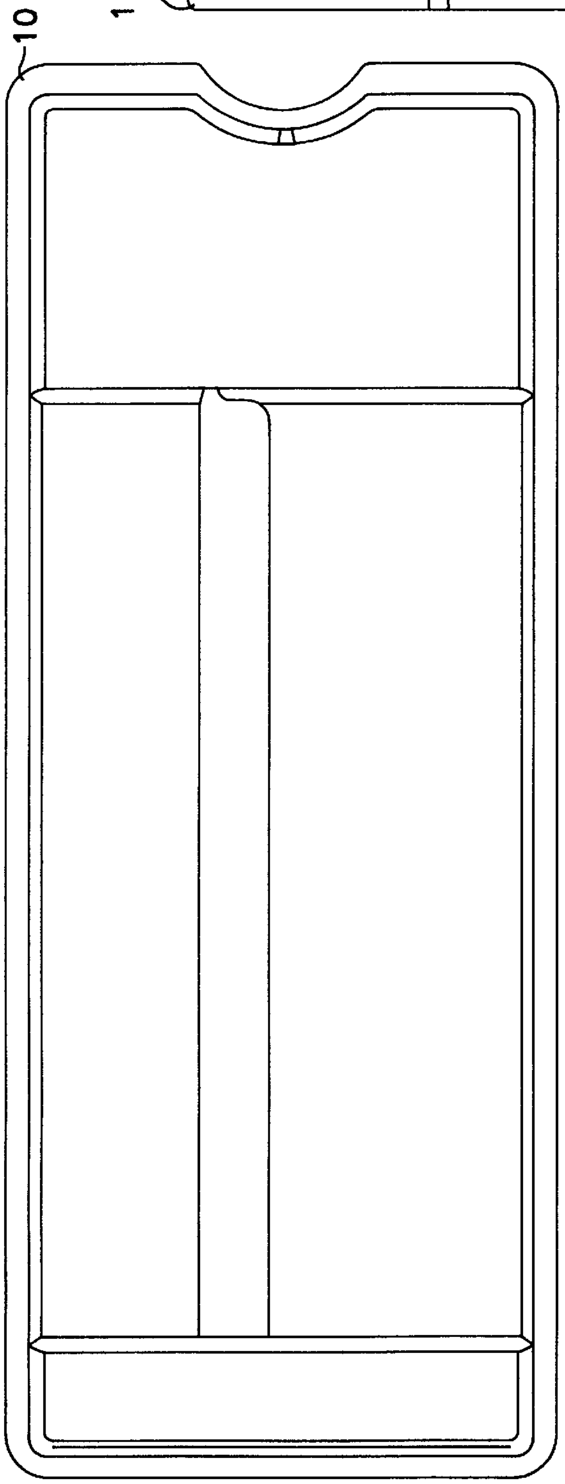
Figure 7B:
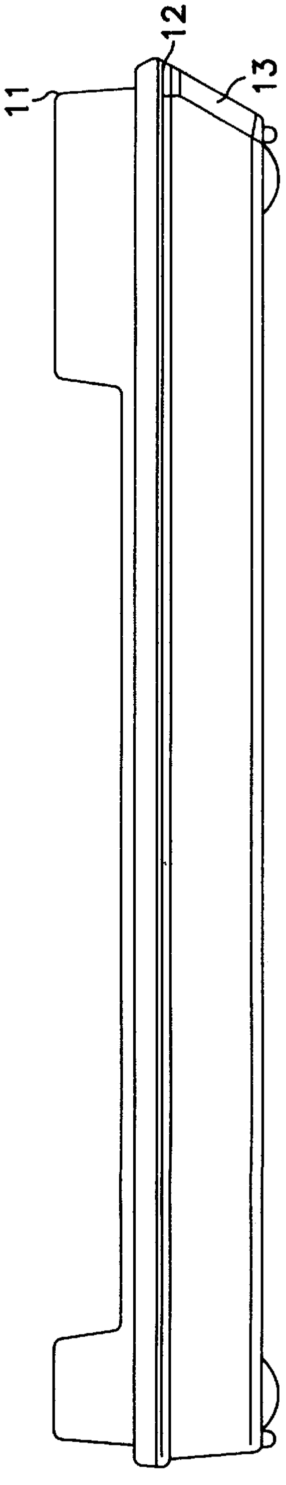

As shown in FIGS. 5A and 5B, the base 13 comprises a planar surface 26 having a plurality of cups 27 and a side wall 28. The walls of the cups 27 extend vertically from a first side of planar surface 26. The side wall 28 extends vertically around the perimeter of the planer surface 26 in the same direction as the walls of the cups 27. The base 13 is constructed of a translucent material which allows light to pass through the cups 27.

As shown in FIG. 5B, various labels or identifying marks are preferably applied or molded into the base 13. These permit the operator of the testing apparatus to more easily identify the test wells.

Figure 3A:
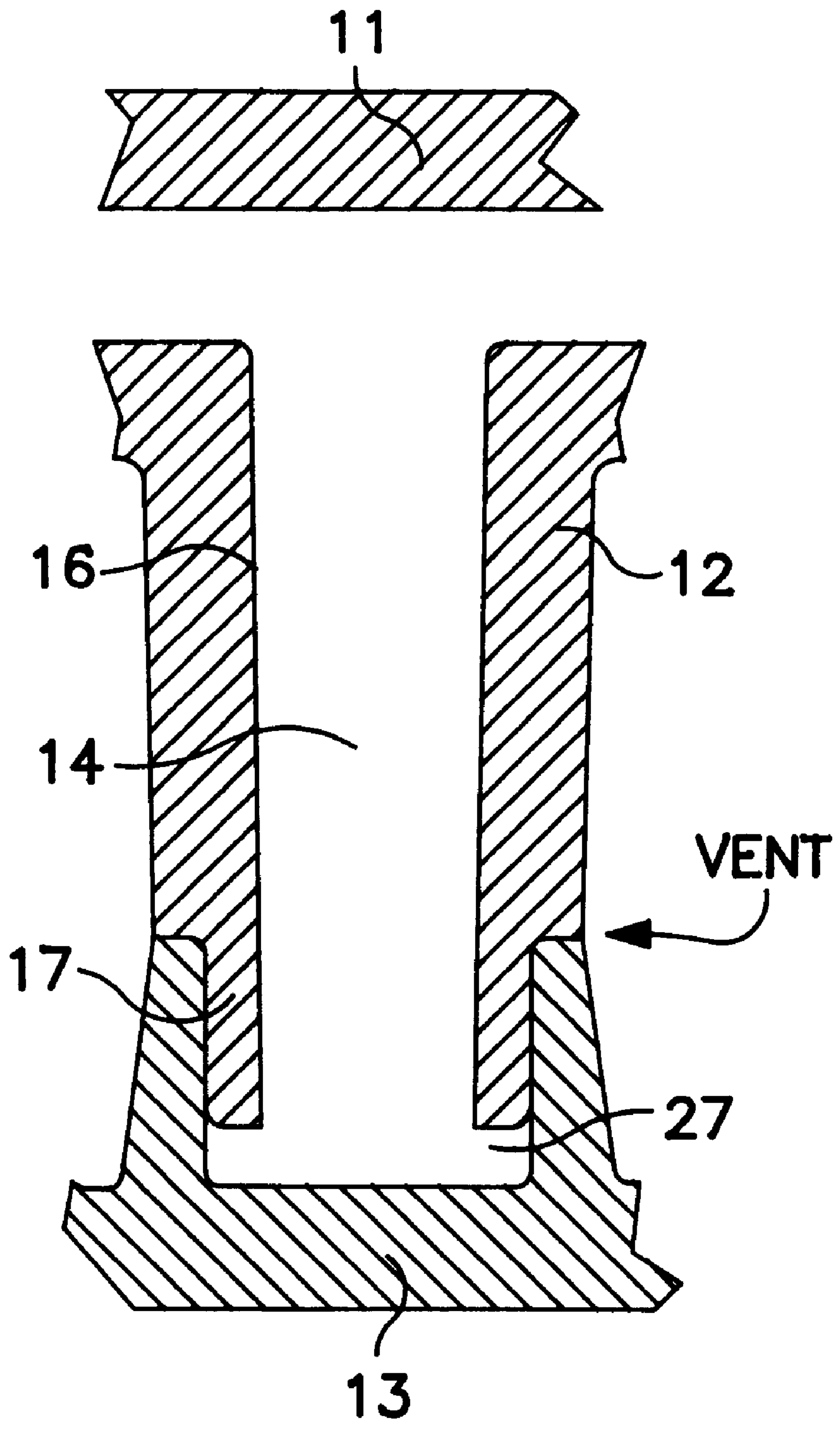
FIG. 3A–3D are cut-away views of one test well within the microbiological test panel assembly of FIG. 1.

Turning to FIG. 3A, when the base 13 and chassis 12 are connected to form the chassis-base subassembly, each test well 14 is formed by the union of the tube 16 with a respective cup 27. The indented band 17 of the tube 16 is inserted into the cup 27. Preferably there is a one-to-one correspondence with each tube 16 and cup 27, where each tube 16 positioned on the chassis 12 so that it is aligned with a respective cup 27. The ribs on the indented portion provide a small air vent between the indented portion and the cup 27 when assembled. This small air vent allows air to escape from the test well when the test well is filled with inocula.

Figure 3B:
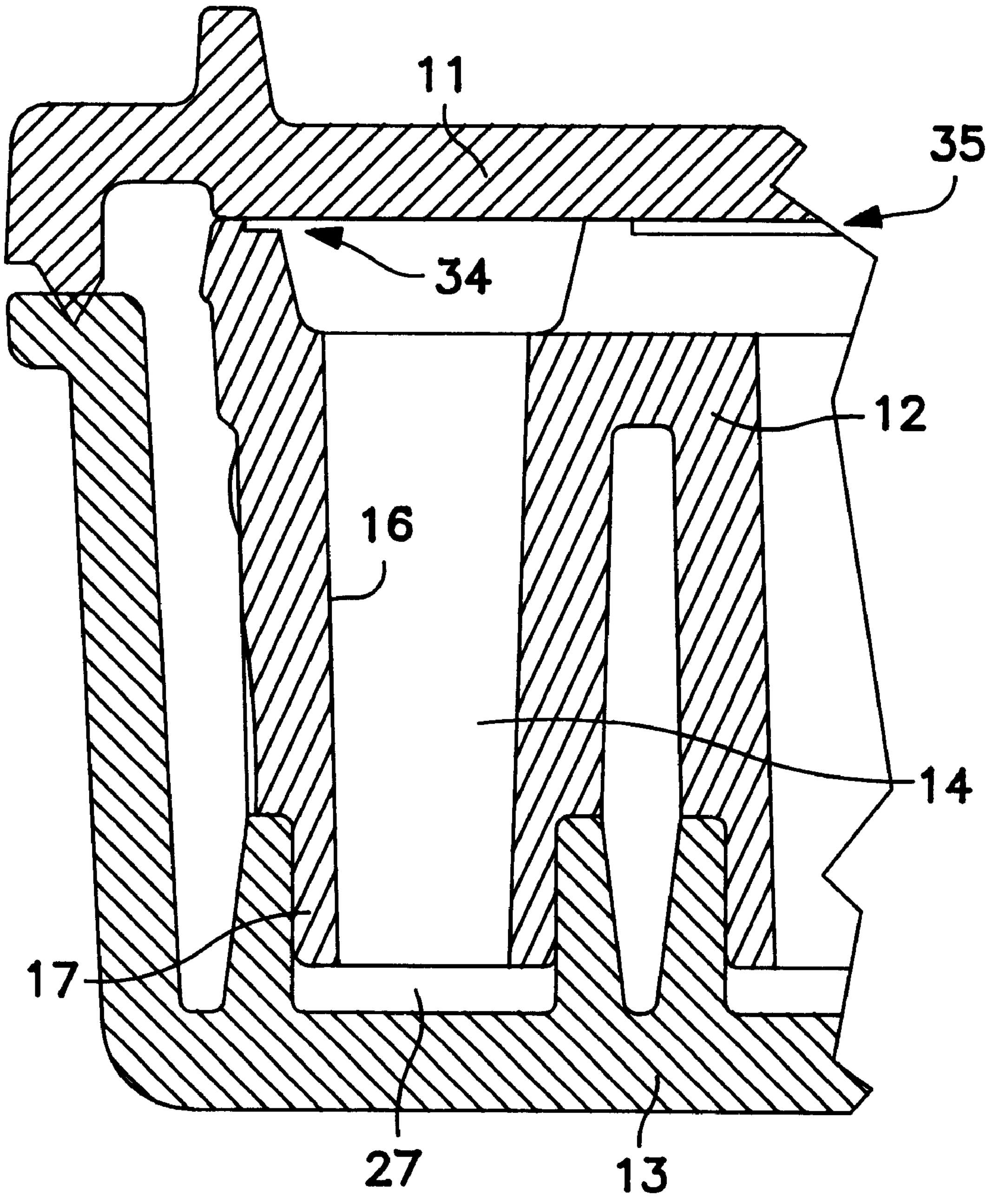

As shown in FIG. 3B, the passage walls 18 of the chassis 12 have a stepped rail 34 which forms a drain gap 35 when the lid 11 is attached to the chassis-base subassembly. The stepped rail 34 is included at both edges of the passage walls 18 that form the serpentine passageways 19. While the lid 11 is in contact with a portion of the stepped rail 34, it is not otherwise secured to the stepped rail 34. The drain gap 35 extends along the entire length of the serpentine passageway 19 from the openings 20 located within the chambers 21 to the opening 22 located at the reservoir 23.

Figure 3C:
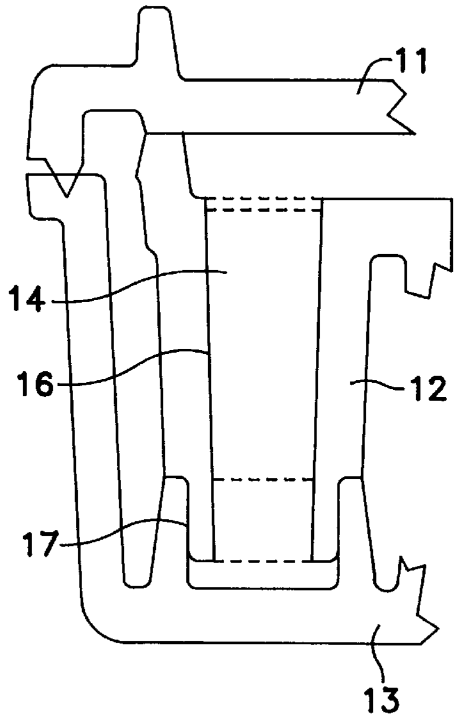
Figure 3D:
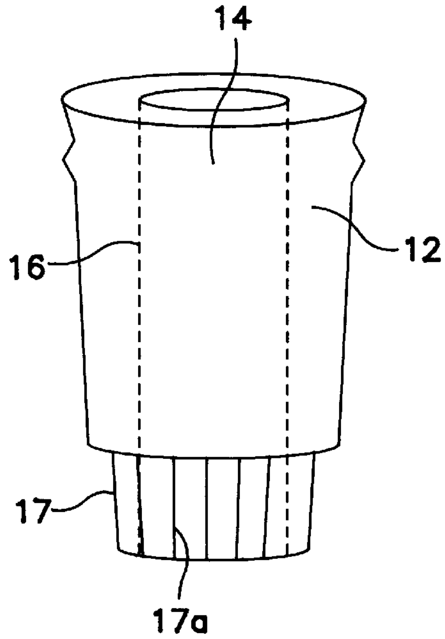

Alternatively, FIG. 3C show the passage walls 18 of the chassis 12 formed without a stepped rail 34 or drain gap 35.

Returning to FIG. 3A, the test wells 14 form, respective enclosures to hold reagents and microbiological samples. These enclosures are were the reactions take place between reagents and the particular microbiological samples inoculated therein. Preferably, the cups 27 may be coated with a dried substrate, therapeutic agent, drug or antibiotic (not shown) in varying concentrations to facilitate various forms of ID and AST tests that may be performed using the test panel assembly 10. Individual cups 27 can contain any one of a variety of substrates, which include for example, adonitol, cellobiose, dextran, insulin, lactitol or maltitol. Of course, other substrates or drugs may be used as will be appreciated in the ID/AST testing unit.

When the cups 27 contain such substrates, the test panel assembly 10 can be classified based on the types of substrates or drugs contained in the cups 27. For example, test panel assembly 10 may be classified as Gram-Positive or Gram-Negative for identification testing. Other classifications may be used for AST testing.

In a preferred embodiment, the test wells 14 are segregated into at least two separate sections. For example the test wells 14 of one section can be used for ID testing and the test wells 14 of the other section can be used for AST testing. As shown in FIG. 1, the test panel assembly 10 includes an ID section 29 and an AST section 30. The ID section 29 consists of fifty-one test wells 14 (as shown in FIGS. 2 and 5A). The AST section 30 consists of eight-five test wells 14. Of course, the number of rows, columns and test wells 14 shown in FIGS. 2 and 5A are merely exemplary and may be changed to suit the requirements of any specific application as will be appreciated by one skilled in the art.

Figure 4A:
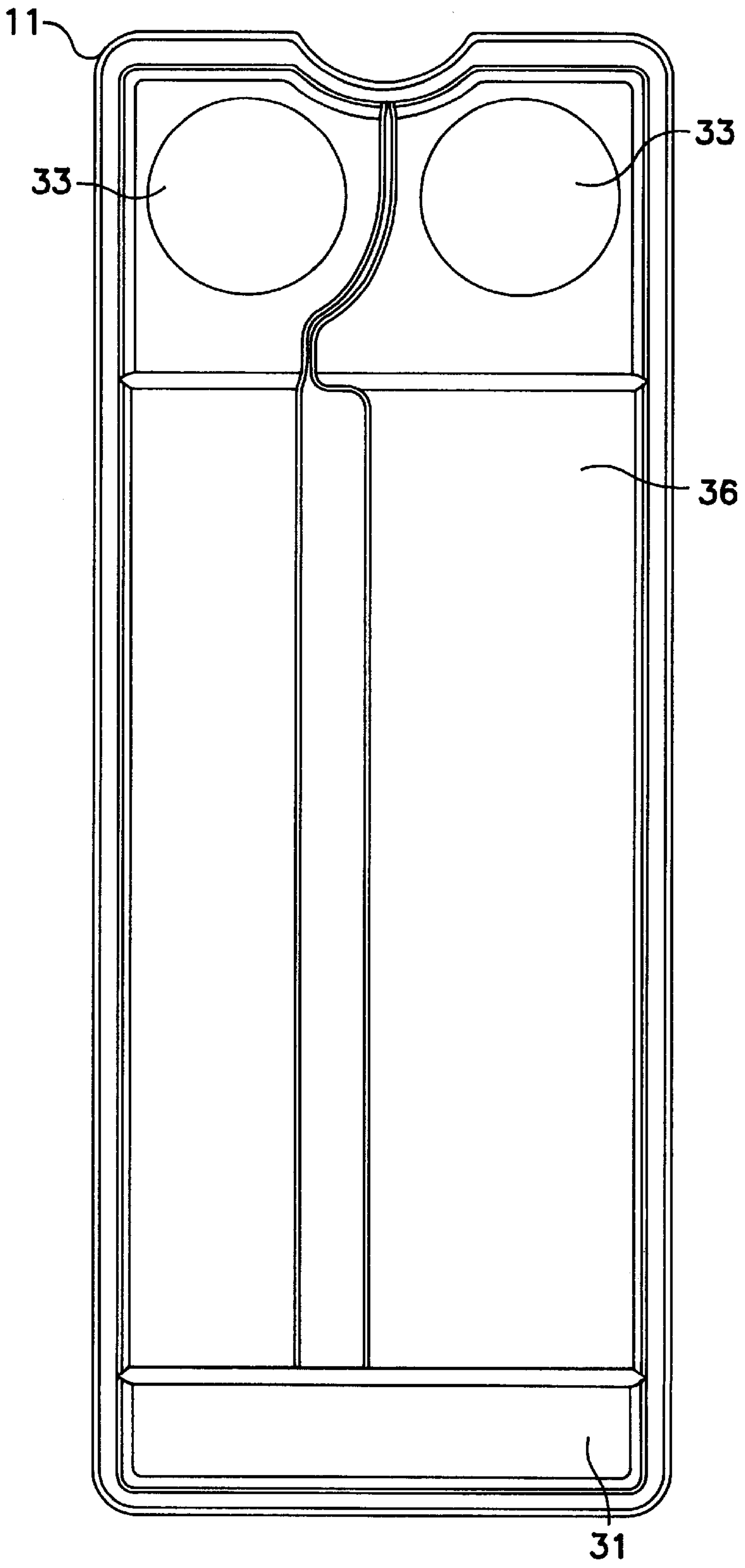
FIGS. 4A and 4B are top and bottom views of the lid of the present invention.
Figure 4B:
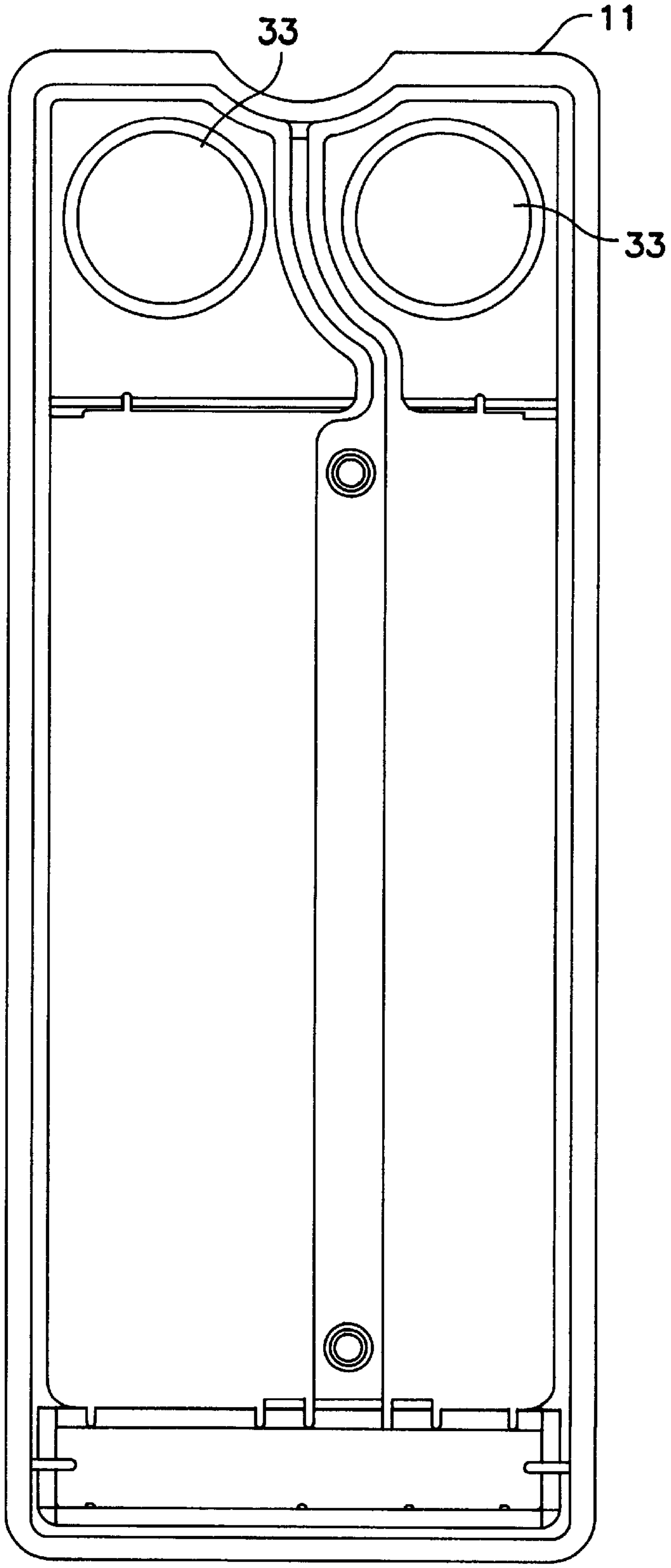

Turning to FIG. 4, the lid 11 comprises a planar surface 36, and protruding sections 31 and 32 (shown in perspective in FIGS. 1 and 6A–I). As discussed above, when the lid 11 is connected to the chassis-base subassembly, section 32 forms the respective chambers 21. A plurality of fill ports 33 are formed in section 32 of the lid 11. One fill port 33 is provided for each chamber 21. The fill ports 33 provide access, via the respective chambers 21, to the serpentine passageways 19.

Preferably section 31 of the lid serves two purposes. First, section 31 provides a top which encloses the reservoir 23 (and enclose the pad 25 in one embodiment). Second, section 31 may be used to mount the test panel assembly 10 in an automated microbiological testing system (not shown). The protruding section 31 may be adapted to insert into panel carriers (not shown) of the automated microbiological testing system so that the test panel assembly 10 is supported therein. As will be appreciated by one skilled in the art, other means of mounting or connecting the test panel assembly 10 to an automated microbiological testing system can be used. For example, flanges, locking pins, mounting hooks, etc., can be used for this purpose.

As discussed above, the chassis-base subassembly is press-fit together. With regard to the lid 11, the perimeter of the lid 11 is pressed into a grove around the perimeter of the base 13 and ultrasonically welded to the base 13 to form an air-tight seal. Of course other methods of assembling the chassis-base subassembly and lid can be used as will be appreciated by one skilled in the art. When the lid 11 is connected, the planer surface 36 of the lid 11 provides a cover over the test wells 14. Preferably, the lid 11 is made of a transparent or translucent material to allow light from the testing apparatus to pass therethrough.

The test panel assembly 10 also includes a panel label (not shown). The panel label can be used to provide a technician, for example, with information related to a particular test panel assembly 10. Additionally, panel labels may be used to identify the complete manufacturing history of the particular test panel assembly 10, to provide information related to the test panel assembly type, and to provide a unique sequence number for identification purposes. In one preferred embodiment the panel label is in a barcode format. The barcode label can be provided in Code 128, numeric format or any other suitable barcode format.

In practice, the test wells 14 of the test panel assembly 10 are inoculated with a broth-suspended microorganism so that reactions can take place. For example, one inocula could be used for ID testing, while another inocula could be used for AST testing, or the same inocula may be used in both sides of the test panel.

To inoculate the test panel assembly 10, the test panel assembly 10 is inclined with respect to the horizontal plane such that the fill ports 33 are elevated. The test panel assembly 10 should be inclined at an angle between 5–45 degrees from the horizontal to ensure proper fill of each test well 14. Preferably, the angle of inclination should be between 20–25 degrees. Separate or the same inocula are added manually to the respective fill ports 33, which cause the respective chambers 21 to fill. The inocula enter the serpentine passageways 19 via the opening 20. Each test well 14 in the ID section 29 and the AST section 30 is inoculated as the inoculum flows down the serpentine passageways 19, toward the reservoir 23 and the pad 25. Gravity drives the inocula through the test panel assembly 10 filling all of the test wells 14 as the liquid front progresses. Excess inoculum flows past the test wells 14 into the reservoir 23 (and is absorbed by the pad 25 in one embodiment). This leaves each filled test well 14 isolated from its neighbors.

The relatively larger height of the test wells to the width of the test wells, as well as the surface tension of the inoculum, prevents the inoculum from escaping once each test well 14 has been filled. The height-width ratio should be at least two-to-one. This also permits the cups 27 of the base 13 to be coated with a dried drug or substrate without cross-talk problems during fill.

After the main flow of inoculum passes the test wells 14, the film of inoculum left on the passage walls 18 of the serpentine passages 19 may attempt to gather into droplets and pool above the filled test wells. If this were to happen, contamination between adjacent test wells 14, or dilution of the test wells could occur. However, this is prevented by the drain gap 35, which wicks this excess inoculum toward the pad 25.

Capillary action draws the excess inoculum down the drain gap 35. The stepped rail 34 maintains the drain gap 35 between the lid 11 and the chassis 12, as well as preventing leakages.

As the test wells 14 are filled with inocula, air trapped within the test well 14 escapes through the small space formed by the vertical ribs of the indented band 17 and the cups 27. This small space is an air vent for each test well 14 which allows trapped air to escape, but is small enough to prevent inocula from escaping. This air then travels through the air communication ports, or snorkels 24, into the chambers 21 formed by section 32 of the lid 11 and the chassis-base subassembly and exits via the fill ports 33.

The test panel assembly 10 can be inoculated at a panel inoculation station (not shown) adapted to support the test panel assembly 10 at the proper incline, or by a person physically holding the test panel assembly at the proper incline while pouring the inocula into the fill ports 33.

While the present invention has been described above in terms of specific embodiments, it is to be understood that the invention is not intended to be confined or limited to the embodiments disclosed herein. On the contrary, the present invention is intended to cover various methods, structures and modifications thereof included within the spirit and scope of the appended claims.

What is claimed is:

1. A microbiological test panel assembly, comprising:

a base comprising a planar surface having a plurality of translucent cups extending from a first side of said planar surface, and a side wall extending from said first side in the same direction as said cups;

a chassis comprising a planar surface having a plurality of open-ended tubes formed on a first side of said chassis, a bottom end of each said tube located on said planar surface, a top end of each said tube having an indented portion for engaging a respective one of said translucent cups so as to form a well when said chassis is press-fit into said base to form a chassis-base subassembly, said chassis also comprising a plurality of raised passage walls on a second side of said planar surface, said passage walls forming a passageway over the openings at the bottom ends of the tubes, one end of the passageway having an opening to allow an inoculum to pass through said passageway, the other end of the passageway having an opening to allow excess inoculum to a reservoir formed at a first end of said chassis, said chassis also comprising an air communication port between said first side and said second side of said planar surface of said chassis, said air communication port formed as an open-ended tube extending from said second side of said planar surface; and a lid attached to said chassis-base subassembly over said second side of said chassis so as cover said chassis-base assembly, said lid comprising a planar surface for covering said plurality of wells, and a fill port at a first end of said lid for receiving the inoculum into said passageway.

2. A microbiological test panel assembly according to claim 1, further comprising:

means for mounting said test panel assembly onto a testing apparatus.

3. A microbiological test panel assembly according to claim 1, wherein said plurality of wells are arranged in an array.

4. A microbiological test panel assembly according to claim 1, wherein the passageway is arranged over the openings at the bottom ends of the tubes of said chassis in a serpentine fashion.

5. A microbiological test panel assembly according to claim 1, wherein said passage walls have a stepped rail formed thereon, so that a drain gap is formed between said planar surface of the lid and said passageway when said lid is attached to said chassis-base subassembly.

6. A microbiological test panel assembly according to claim 1, wherein said indented portion of each said tube of said chassis has formed thereon a plurality of ribs extending in the same direction as said tube.

7. A microbiological test panel assembly according to claim 1, wherein said lid is formed from a translucent material.

8. A microbiological test panel assembly according to claim 1, wherein said chassis is constructed from an opaque material.

9. A microbiological test panel assembly according to claim 1, wherein said chassis further comprises an absorbing member positioned in said reservoir for absorbing the excess inoculum.

10. A microbiological test panel assembly according to claim 9, wherein said absorbing member is constructed from an cellulose acetate material.

11. A microbiological test panel assembly according to claim 9, wherein said lid further comprises a reservoir at a second end of said lid for receiving said absorbing member of said chassis.

12. A chassis of a test panel, comprising:

a planar surface having a first side and a second side;

a plurality of open-ended tubes, each having a bottom and a top end, formed on said first side of said planar surface, said bottom end of each said tube located on said planar surface, each said tube extending from said planar surface, and said top end of each said tube having an indented portion;

a reservoir formed at a first end of said planar surface;

a plurality of raised passage walls on a second side of said planar surface, said passage walls forming a passageway over the openings at the bottom ends of said tubes, one end of the passageway having an opening to allow a liquid to flow through said passageway, the other end of the passageway having an opening to allow excess liquid to flow to said reservoir; and an air communication port between said first side and said second side of said planar surface, said air communication port formed as an open-ended tube extending from said second side of said planar surface.

13. A microbiological test panel assembly, comprising:

a base comprising a planar surface having a plurality of translucent cups extending from a first side of said planar surface, and a side wall extending from said first side in the same direction as said cups;

a chassis comprising a planar surface having a plurality of open-ended tubes formed on a first side of said chassis, a bottom end of each said tube located on said planar surface, a top end of each said tube having an indented portion for engaging a respective one of said translucent cups so as to form a well when said chassis is press-fit into said base to form a chassis-base subassembly, said chassis also comprising a plurality of raised passage walls on a second side of said planar surface, said passage walls forming a plurality of passageways, each passageway positioned over a predetermined plurality of openings at the bottom ends of the tubes, one end of each passageway having an opening to allow an inoculum to pass through each said passageway, the other end of each passageway having an opening to allow excess inoculum to a reservoir formed at a first end of said chassis, said chassis also comprising an absorbing member positioned in said reservoir for absorbing the excess inoculum, said chassis also comprising an air communication port between said first side and said second side of said planar surface of said chassis, said air communication port formed as an open-ended tube extending from said second side of said planar surface; and a lid attached to said chassis-base subassembly over said second side of said chassis so as cover said chassis-base assembly, said lid comprising a planar surface for covering said plurality of wells, a reservoir at a first end of said lid for receiving said absorbing member of said chassis, and a plurality of fill ports at a second end of said lid, each said fill port for receiving the inoculum into each respective passageway.

14. A method for inoculating a test panel, the test panel comprising a fill port, a reservoir, a plurality of wells, and a passageway formed over the wells connecting the fill port and the reservoir, said method comprising the steps of:

holding the test panel at a substantially stationary inclined position with respect to a horizontal plane, with the fill port being elevated from the horizontal plane;

inserting inocula into the fill port; and maintaining the test panel in the substantially stationary position to allow the inocula to flow through the passageway to fill the wells and to allow the excess inocula to flow into the reservoir.

15. A method according to claim 14, wherein the incline is at an angle between 20–25 degrees from the horizontal plane.

16. A test panel, comprising:

a planar surface having a first side, a second side, a top end and a bottom end;

a plurality of wells, each of said wells having an open end on said planar surface and another end which prevents a liquid from escaping, said wells extending from said first side of said planar surface;

a reservoir formed at said bottom end of said planar surface;

a fill port at said top end of said planar surface;

a plurality of raised passage walls formed on said second side of said planar surface, said raised passage walls forming a passageway over said open ends of said wells, one end of the passageway having an opening to allow the liquid to flow through said passageway from said fill port, the other end of the passageway having an opening to allow excess liquid to flow to said reservoir; and an air communication port on said planar surface for allowing air to pass from said first side of said planar surface to said second side.

17. A test panel according to claim 16, wherein said another end of each of said wells has a rib for allowing air in said wells to escape.

* * * * *